United States Patent [19]

Inoi et al.

[11] Patent Number: 4,784,853
[45] Date of Patent: Nov. 15, 1988

[54] ANTIVIRAL AGENT

[75] Inventors: Takeshi Inoi, Yokohamashi; Hiroaki Ishibashi, Minamatashi; Etsuro Yoshikawa, Yokohamashi, all of Japan

[73] Assignee: Chisso Corporation, Osaka, Japan

[21] Appl. No.: 45,864

[22] Filed: May 4, 1987

Related U.S. Application Data

[63] Continuation of Ser. No. 649,660, Sep. 12, 1984, abandoned.

[30] Foreign Application Priority Data

Sep. 29, 1983 [JP] Japan .................................. 58-181225

[51] Int. Cl.$^4$ .............................................. A61K 35/78
[52] U.S. Cl. .................................. 424/195.1; 514/888
[58] Field of Search ..................................... 424/195.1

[56] References Cited

PUBLICATIONS

Chem. Abst. 95: 167321d 1981.
Chem. Abstract 106: 173194b, 1986.

Primary Examiner—John Rollins
Attorney, Agent, or Firm—Fred Philpitt

[57] ABSTRACT

An antiviral agent containing as its active ingredient, an ingredient extracted from *Crocosmia x crocosmaeflora* N.E. Br.

16 Claims, No Drawings

ANTIVIRAL AGENT

This is a continuation of application Ser. No. 649,660, filed Sept. 12, 1984 now abandoned and the benefits of 35 USC 120 are claimed relative to it.

BACKGROUND OF THE INVENTION

1. Field of the Invention

This invention relates to an antiviral active substance and more particularly to an antiviral active substance obtained by extracting the whole and particularly the rhizome of *Crocosmia x crocosmaeflora* N.E. Br. (another name: *Tritonia crocosmaeflora Lemoine*).

2. Description of the Prior Art

*Crocosmia x crocosmaeflora* N.E. Br. is a perennial plant belonging to Basellaceae, and not only cultivated in gardens but also often naturally grows at warm places. It has a spherical rhizome at its subterranean part, a height of 50~80 cm and sword-shaped leaves. In summer, it has two or three branches at the upper part of its stem and a number of red flowers open in the form of second spikes in one side. The flower has a diameter of 2~3 cm, and its perianth is infundibular and has 6 pieces. The *Crocosmia x crocosmaeflora* N.E. Br. has been used for appreciation, but has no other difinite uses.

SUMMARY OF THE INVENTION

The present invention has been made based on a knowledge that an ingredient obtained by extracting the whole and particularly the rhizome of *Crocosmia x crocosmaeflora* N.E. Br. exhibits an antiviral activity upon organisms including human beings and is useful. Namely, the present invention resides in an antiviral agent containing as an active ingredient, an ingredient obtained by extracting *Crocosmia x crocosmaeflora* N.E. Br.

DETAILED DESCRIPTION AND THE PREFERRED EMBODIMENTS

The ingredient of the present invention can be obtained from the whole and particularly the rhizome of *Crocosmia x crocosmaeflora* N.E. Br., concretely e.g. by the following method: The whole or the rhizome of *Crocosmia x crocosmaeflora* N.E. Br. or dried materials thereof is subjected to extraction operation with water, lower aliphatic alcohols, water-containing lower aliphatic alcohols, aromatic alcohols or solvents which are hydrophylic to a certain extent and oleophylic to a certain extent, within a temperature range of about 0° C. to boiling point of said water, etc. under the atmospheric pressure or under decreased or increased pressure. Further, the resulting extraction solution may be concentrated into a concentrated extract. If necessary, the raw material, extraction solution or concentrated extract may sometimes be treated with a fat-dissolving solvent such as ethyl acetate, for example, for removing chlorophyll. The thus obtained concentrated extract has an antiviral activity and may be, as it is, used as an active ingredient of the present invention, but if necessary, it may be made into powdery form by various drying measures.

The ingredient of the present invention has a somewhat bitter taste. Further, its concentrated extract and dry powder usually exhibit from a pale yellow color to yellowish brown color. Further they are soluble in water, lower aliphatic alcohols such as methanol, ethanol, propanol, etc. or water-containing materials thereof.

The ingredient of the present invention may be used in the form of composition for oral administration, injections for parenteral administration and external preparations. Namely, vehicles, distilled water, higher alcohols surfactants, etc. which are known in the field of the art may be used.

Examples will be described below, but the present invention is not intended to be limited thereto.

EXAMPLE 1

The rhizome (350 g) of naturally growing *Crocosmia x crocosmeaflora* N.E. Br. was milled and water (2,000 ml) was added, followed by extracting it with stirring at its boiling point for 90 minutes, filtering, allowing the filtrate to stand overnight, separating the resulting white precipitate and concentrating the residual solution at 80° C. under reduced pressure to about 150 ml. When white precipitate was formed at this time, it was filtered off, followed by carrying out freeze-drying to obtain a brown dry ingredient (2.7 g).

The resulting dry ingredient consists of a mixture and its elemental analysis values are shown below for reference (unit: % by weight):
C: 42.0, H: 5.7, N: 1.5.

EXAMPLE 2

The rhizome (1 Kg) of cultivated *Crocosmia x crocosmaeflora* N.E. Br. was milled and ethyl acetate (3 l) was added, followed by stirring at about 20° C. for 2 hours, filtering, washing the resulting solid matter with a small amount of water, air-drying, adding ethanol (6 l) to the air-dried solid matter, extracting it with stirring at 50° C. for 2 hours, filtering the extraction solution, concentrating the filtrate to dryness at 60° C. under reduced pressure, adding water (1 l), filtering off the resulting fine white precipitates, and concentrating the filtrate to dryness at 80° C. under reduced pressure to obtain a yellowish brown dry ingredient (21.1 g).

The dry ingredient consists of a mixture, and its elemental analysis values are shown below for reference (unit: % by weight):
C: 42.2, H: 6.8, N: 0.1.

EXAMPLE 3

The whole of naturally growing *Crocosmia x crocosmaeflora* (1 Kg) was slit and ethyl acetate (3 l) was added, followed by stirring at about 20° C. for 4 hours, filtering, washing the solid matter with a small amount of water, air-drying, adding ethanol of 80% by volume (20% of which was water) (6 l), extracting with stirring at 60° C. for 2 hours, filtering, concentrating the filtrate at 60° C. under reduced pressure to about 300 ml, cooling down to room temperature, filtering off the resulting solid matter and concentrating the filtrate to dryness at 80° C. to obtain a dry ingredient (18.4 g).

The thus obtained dry ingredient consists of a mixture and its elemental analysis values are shown below for reference (unit: % by weight):
C: 42.1, H: 6.6, N: 1.1.

EXAMPLE 4

Example 2 was repeated except that ethanol (6 l) was replaced by methanol (6 l) to obtain a yellow dry ingredient (24.0 g).

This dry ingredient consists of a mixture, and its elemental analysis values are shown below for reference (unit: % by weight).

C: 50.3, H: 8.2, N: 0.9.

The inhibitory effect of the extract ingredients obtained in the above Examples, upon influenza virus was observed according to a biological method. Further, the infection inhibitory effect thereof upon plant viruses was also inspected.

REFERENCE EXAMPLE 1

A. Test Materials (1) Preparation of specimen and sample

The extract dry ingredient obtained in Example 1, as a specimen, was weighed and (1/100 mol)/l PBS (phosphate buffer saline) (−) (pH 7.2) was added, followed by heating the mixture in hot water at 100° C. for 30 minutes and diluting the resulting solution as a stock solution (1.6% solution) at 7 stages according to binary dilution method to prepare samples.

(2) Grown hen's egg

Eleven-days old, grown hen's eggs of white leghorn SPF hen group (Line-S) were used.

(3) Influenza virus

Influenza virus A/Kumamoto/37/79 strains was used after its viral value was measured by means of grown hen's eggs.

B. Testing Method and Results (1) Toxicity of specimen upon hen's egg

Samples prepared so as to give concentrations of 1.6~0.025% were inoculated into the respective allantoic vesicles of 10 eleven-days old grown hen's eggs, each concentration, in an amount of 0.1 ml, followed by culture at 34°±1° C. for 5 days. The presence or absence of toxicity was judged from life or death during 5 days culture, excluding dead eggs within 24 hours after the inoculation.

The results are shown in Table 1. As seen from this Table, no death was observed with any group inoculated with the samples having the above concentrations of 1.6% (highest) to 0.025%. From these results, it was judged that there was no toxicity of the specimen upon grown hen's eggs.

(2) Inactivation effect of specimen upon virus

①Test according to a method of sensitization time, unchanged/virus.specimen concentration, varied.

Viral solutions diluted to $10^{6.0}$ ~ $10^{2.0}$ EID$_{50}$/0.1 ml, each in an amount of 3 ml were mixed with samples each in an amount of 3 ml. After sensitization at room temperature (22° C.) for 10 minutes, the respective mixed solutions were inoculated into 10 eleven-days old grown hen's eggs in an amount of 0.1 ml, followed by culture at 34°±1° C. for 3 days to observe the hemagglutination activity (HA) of the allantoic vesicle liquid. In this case, the hemagglutination activity (HA) test was carried out by adding a 0.5% hen's erythrocyte suspension (0.4 ml) into the allantoic vesicle of grown hen's eggs, followed by shaking, sensitizing at room temperature for 40 minutes and judging the presence or absence of agglutination.

The results are shown in Table 2. From this Table, a viral inactivation effect of 22% was observed upon the virus in an amount of $10^{2.0}$ EID$_{50}$/0.1 ml with 0.05% solution, whereas only a viral inactivation effect of 20% was observed upon the virus in an amount of $10^{5.0}$ EID$_{50}$/0.1 ml with 0.8% solution.

②Test according to a method of viral amount, unchanged/specimen concentration sensitization time, varied.

In view of the above results, the viral solution of $10^{4.0}$ EID$_{50}$/0.1 ml was choiced and the viral inactivation effects at the respective concentrations with lapse of time were observed.

The results are shown in Table 3. From this table, the growth inhibitory effect of 0.2% solution in a viral amount of $10^{4.0}$ EID$_{50}$/0.1 ml was 20% in terms of the sensitization time of the virus and the specimen in the case of 10 minutes; 30%, in the case of 30 minutes; and 70%, in the case of 60 minutes. Such a sensitization time-dependent inactivation effect was also observed in the case of specimens having other concentrations.

C. Conclusion

From the above inactivation tests of the extract ingredient obtained in Example 1 upon influenza virus, with grown hen's eggs, the following conclusion was obtained:

(1) The specimen exhibited no toxicity upon 11-days old grown hen's eggs.

(2) The specimen exhibited a viral concentration- and sensitization time-dependent inactivation effect upon influenza virus.

TABLE 1

| Toxicity of extract ingredient obtained in Example 1 upon grown hen's egg[1] | |
|---|---|
| Specimen concentration (%) | Toxicity[2] |
| 1.6 | 0/10 |
| 0.8 | 0/10 |
| 0.4 | 0/9 |
| 0.2 | 0/10 |
| 0.1 | 0/10 |
| 0.05 | 0/9 |
| 0.025 | 0/9 |

[1]0.1 ml of specimen was inoculated into the respective eleven-days old grown hen's eggs, followed by culture at 34 ± 1° C. for 5 days and then judged.
[2]Number of dead grown hen's eggs/number of inoculated grown hen's eggs.

TABLE 2

Inactivation test results of extract ingredient obtained in Example 1, upon influenza virus (1)[1]

| Viral amount (EID$_{50}$/0.1) | Viral growth in the presence of specimens having various concentrations (%)[2] | | | | | | |
|---|---|---|---|---|---|---|---|
| | Concentration (%) | | | | | | |
| | 0.8 | 0.4 | 0.2 | 0.1 | 0.05 | 0.025 | 0.0125 |
| $10^{6.0}$ | 10/10 | 10/10 | 10/10 | 9/9 | 10/10 | 10/10 | 10/10 |
| $10^{5.0}$ | 8/10 | 10/10 | 10/10 | 10/10 | 10/10 | 10/10 | 9/9 |
| $10^{4.0}$ | 4/9 | 5/10 | 6/9 | 10/10 | 10/10 | 10/10 | 10/10 |
| $10^{3.0}$ | 0/10 | 0/10 | 4/10 | 3/10 | 10/10 | 10/10 | 9/9 |

TABLE 2-continued

Inactivation test results of extract ingredient obtained in Example 1, upon influenza virus (1)[1]

| Viral amount ($EID_{50}/0.1$) | Viral growth in the presence of specimens having various concentrations (%)[2] Concentration (%) | | | | | | |
|---|---|---|---|---|---|---|---|
| | 0.8 | 0.4 | 0.2 | 0.1 | 0.05 | 0.025 | 0.0125 |
| $10^{2.0}$ | 0/10 | 0/10 | 0/10 | 1/10 | 7/9 | 10/10 | 10/10 |

[1]Viral solutions having various concentrations (3 ml) were mixed with specimens having various concentrations (3 ml), followed by sensitization at room temperature for 10 minutes.
[2]Number of HA-positive grown hen's eggs/number of inoculated grown hen's eggs.

TABLE 3

Inactivation test results of extract ingredient obtained in Example 1 upon influenza virus (2)[1]

| Sensitization time (min.) | Viral growth in the presence of specimens having various concentrations (%)[2] Concentration (%) | | | | | | |
|---|---|---|---|---|---|---|---|
| | 0.8 | 0.4 | 0.2 | 0.1 | 0.05 | 0.025 | 0.0125 |
| 5 | 9/10 | 10/10 | 10/10 | 9/9 | 10/10 | 10/10 | 10/10 |
| 10 | 4/10 | 6/10 | 8/10 | 10/10 | 10/10 | 10/10 | 10/10 |
| 30 | 1/10 | 2/10 | 7/10 | 10/10 | 10/10 | 10/10 | 9/9 |
| 60 | 0/10 | 2/10 | 3/10 | 9/10 | 9/9 | 10/10 | 10/10 |

[1]Viral solution of $10^{4.0}$ $EID_{50}/0.1$ ml (3 ml) were mixed with specimens having various concentrations (3 ml), followed by sensitization at room temperature for the above listed times.
[2]Number of HA-positive grown hen's eggs/number of inoculated grown hen's eggs.

REFERENCE EXAMPLE 2

A. Materials and method (1) Specimen

The extract ingredient obtained in Example 2, as a specimen, was weighed in amounts of 0.30 g (the first test) and 0.10 g (the second test), and (1/100 mol)/l PBS(−) (pH 7.2) was added, followed by dissolution and dilution to prescribed concentrations to prepare samples.

(2) Grown hen's egg

Eleven-days old grown hen's eggs of white leghorn SPF hen's group (Line S) were used for tests.

(3) Influenza virus

Influenza virus A/Kumamoto/37/79 strains shared from National Institute of Health of Japan was used. The infection value of this stock solution was $10^{8.7}$ $EID_{50}/0.1$ ml.

(4) Preliminary test (Toxicity test upon hen's embryo)

Specimens diluted to 1.6% (62.5 times)~0.05% (2,000 times) according to binary dilution method were inoculated into the respective allantoic vesicles of 10 eggs, each concentration, in an amount of 0.1 ml, followed by culture at 34°±1° C. for 4 days, during which the inoculated eggs were inspected every day to record their life and death.

(5) Inactivation test of specimens upon influenza virus

To the respective specimens (each, 15 ml) diluted to 0.4% (250 times)~0.003125% (32,000 times) according to binary dilution method was added the viral solution of $10^{6.7}$ $EID_{50}/0.1$ ml in an equal amount, followed by sensitization at room temperature (28° C.) for 5, 10, 30 and 60 minutes and then measuring the viral infection values in the respective mixed solutions according to egg inoculation method.

B. Results (1) Toxicity of specimens upon eggs

As shown in Table 4, as to eggs inoculated with the specimen solutions of 1.6 and 0.8%, the whole was dead within 24 hours after the inoculation, and as to eggs inoculated with 0.4% solution, 7 eggs (70%) was dead within 48 hours. As to eggs inoculated with specimens of further lower concentration, the whole survived excluding one example (eggs inoculated with 0.1% solution). As to these dead eggs, in order to confirm whether they were dead due to bacterial infection, bacterial culture was carried out. The results are shown in Table 5. As seen from the Table, no alive bacteria could be detected in any of the dead eggs.

(2) Inactivation effect of specimens upon influenza virus

Test was carried out first using specimens having final concentrations of 0.4~0.025%. As a result, as shown in Tables 6 and 8, almost the same viral inactivation tendencies were observed in the presence of specimens of any concentrations tested, and in the case of the sensitization times of 30 minutes or longer, no infective virus could be detected in the total examples and the minimum effective dose could not be measured. Thus, as the second test, similar tests were carried out in the presence of specimens having final concentrations of 0.025~0.003125%. As a result, as shown in Tables 7 and 8, almost the same results as those of the first test were obtained in the presence of specimen of 0.025% concentration to confirm the reproducibility of the test. The inactivation effect of specimens upon the virus was observed down to 0.0125% concentration to a similar extent to that observed in the presence of specimens having higher concentrations than the above. However, in the presence of specimens having lower concentrations than 0.00625%, the viral values after the respective sensitization times became clearly higher to observe the limit of the inactivation effect.

C. Conclusion

The extract ingredient obtained in Example 2 exhibited a considerably powerful lethal effect upon the eggs as compared with that obtained in Example 1. This was considered to be due to the toxicity of the specimens since the results of the bacterial culture of dead eggs were negative in all the examples. When 50% lethal dose ($ELD_{50}$) of the specimens were sought according to graphical analysis, it was about 0.33 mg/egg, that is, in this test, too, the lethal effect was observed in almost the same concentration as the above.

On the other hand, the inactivation effect of the specimens upon influenza virus was observed in a high dilution exceeding the concentration at which the toxicity was exhibited. The inactivation effect naturally varies depending on whether the sensitization time is long or short, but in the case of a sensitization time of 30 minutes, it was regarded that most of influenza viruses were inactivated in the presence of the specimen of 0.0125% (0.0125 mg/egg).

TABLE 4

Toxicity of extract ingredient obtained in Example 2, upon grown hen's eggs

| Specimen[1] concentration (%) | Death of grown hen's eggs[2] Days after inoculation | | | | | |
|---|---|---|---|---|---|---|
| | 1 | 2 | 3 | 4 | Total | % |
| 1.6 | 10 | — | — | — | 10 | 100 |
| 0.8 | 10 | — | — | — | 10 | 100 |
| 0.4 | 6 | 1 | 0 | 0 | 7 | 70 |
| 0.2 | 0 | 0 | 0 | 0 | 0 | 0 |
| 0.1 | 1 | 0 | 0 | 0 | 1 | 10 |
| 0.05 | 0 | 0 | 0 | 0 | 0 | 0 |

[1]Specimens of various concentrations were inoculated in 0.1 ml/egg. Thus the amount of practically inoculated specimens is 1.6 mg/egg in the case of 1.6%.
[2]Inoculated into 10 eggs each concentration. Numeral figure represents number of dead eggs.

TABLE 5

Bacterial culture test with dead eggs in toxicity test

| Specimen concentration (%) | Positive proportion in bacterial culture[1] Culture temperature: | | Judgement |
|---|---|---|---|
| | 22° C. | 37° C. | |
| 1.6 | 0/10 | 0/10 | Negative |
| 0.8 | 0/10 | 0/10 | Negative |
| 0.4 | 0/7 | 0/7 | Negative |
| 0.1 | 0/1 | 0/1 | Negative |

[1]The allantoic vesicle liquids of the respective dead eggs were taken, and each liquid eas inoculated into two thioglycol media (20 ml) in an amount of 1 ml, each of these being cultured at prescribed culture temperature for 10 days. Positive number in bacterial culture/number of cultured eggs (number of dead eggs)

TABLE 6

Influenza virus-infection value in specimen solutions of various concentrations (1)

| Specimen[1] concentration (%) | Sample dilution after sensitization (log) | Number of hemagglutination positive eggs/number of inoculated eggs Sensitization time (min.) | | | |
|---|---|---|---|---|---|
| | | 5 | 10 | 30 | 60 |
| 0.4 | 0 | — | 0/2 | 0/3 | 0/2 |
| | −1 | — | 2/10 | 0/10 | 0/8 |
| | −2 | 10/10 | 2/10 | 0/10 | 0/10 |
| | −3 | 8/10 | — | — | — |
| | −4 | 1/10 | — | — | — |
| 0.2 | 0 | — | 0/7 | 0/8 | 0/8 |
| | −1 | — | 3/10 | 0/10 | 0/10 |
| | −2 | 9/10 | 3/10 | 0/10 | 0/10 |
| | −3 | 7/10 | — | — | — |
| | −4 | 0/10 | — | — | — |
| 0.1 | 0 | — | — | 0/9 | 0/10 |
| | −1 | — | 7/10 | 0/10 | 0/9 |
| | −2 | 9/10 | 2/10 | 0/10 | 0/10 |
| | −3 | 6/10 | 0/10 | — | — |
| | −4 | 0/10 | — | — | — |
| 0.05 | 0 | — | — | — | 0/9 |
| | −1 | — | 7/10 | 0/10 | 0/10 |
| | −2 | 10/10 | 5/10 | 0/10 | 0/10 |
| | −3 | 9/9 | 1/10 | 0/10 | — |
| | −4 | 3/9 | — | — | — |
| 0.025 | 0 | — | — | — | 0/10 |
| | −1 | — | 8/10 | 0/10 | 0/10 |
| | −2 | 10/10 | 1/10 | 0/10 | 0/10 |
| | −3 | 8/9 | 0/9 | 0/10 | — |
| | −4 | 2/10 | — | — | — |
| Control[2] | −4 | 5/5 | 5/5 | 5/5 | 5/5 |
| | −5 | 5/5 | 4/4 | 5/5 | 4/5 |
| | −6 | 4/5 | 4/5 | 5/5 | 4/4 |
| | −7 | 2/5 | 1/5 | 0/5 | 0/5 |

[1]Specimen concentration is expressed in terms of concentration after mixing of specimen with viral solution in equal amounts.
[2]Control represents a mixture of viral solution with PBS (−).

TABLE 7

Influenza virus-infection value in specimen solutions of various concentrations (2)

| Specimen[1] concentration (%) | Sample dilution after sensitization (log) | Number of hemagglutination positive eggs/number of inoculated eggs Sensitization time (min.) | | | |
|---|---|---|---|---|---|
| | | 5 | 10 | 30 | 60 |
| 0.025 | 0 | — | — | 0/10 | 0/9 |
| | −1 | 9/9 | 2/10 | 0/9 | 0/10 |
| | −2 | 9/10 | 0/10 | 0/10 | 0/10 |
| | −3 | 5/10 | 0/10 | — | — |
| 0.0125 | −1 | — | — | 0/10 | 0/10 |
| | −2 | 10/10 | 0/10 | 0/10 | 0/10 |
| | −3 | 5/10 | 0/10 | 0/9 | 0/10 |
| | −4 | 0/10 | 0/10 | — | — |
| 0.00625 | −1 | — | — | 8/10 | 0/10 |
| | −2 | — | 7/10 | 3/10 | 0/10 |
| | −3 | 9/10 | 4/10 | 0/10 | 0/10 |
| | −4 | 2/10 | 0/10 | — | — |
| | −5 | 0/10 | — | — | — |
| 0.003125 | −1 | — | — | 10/10 | 10/10 |
| | −2 | — | — | 10/10 | 10/10 |
| | −3 | 10/10 | 10/10 | 8/10 | 5/10 |
| | −4 | 10/10 | 10/10 | — | — |
| | −5 | 4/10 | 5/10 | — | — |
| Control[2] | −4 | 5/5 | 5/5 | 5/5 | 5/5 |
| | −5 | 5/5 | 4/4 | 5/5 | 5/5 |
| | −6 | 4/5 | 5/5 | 4/5 | 3/5 |
| | −7 | 0/5 | 0/5 | 0/4 | 0/4 |

[1]Specimen concentration is expressed in terms of concentration after mixing of specimen with viral solution in equal amounts.
[2]Control represents a mixture of viral solution with PBS (−).

TABLE 8

Change with lapse of time of influenza virus-infection value in specimen solutions of various concentrations

| Specimen[1] concentration (%) | Viral infection value (log $EID_{50}/0.1$ ml) Sensitization time (min.) | | | |
|---|---|---|---|---|
| | 5 | 10 | 30 | 60 |
| 0.4 | 3.40 | 0.90 | ND[2] | ND |
| 0.2 | 3.10 | 1.10 | ND | ND |
| 0.1 | 3.00 | 1.40 | ND | ND |
| 0.05 | 3.83 | 1.80 | ND | ND |
| 0.025 | 3.60 | 1.40 | ND | ND |
| 0.025 | 2.90 | 0.70 | ND | ND |
| 0.0125 | 3.00 | ≦1.50 | ≦0.50 | ≦0.50 |
| 0.00625 | 3.60 | 2.60 | 1.60 | ≦0.50 |
| 0.003125 | 4.90 | 5.00 | 3.30 | 3.00 |
| Control[3] | 6.70 | 6.50 | 6.50 | 6.30 |
| | 6.30 | 6.50 | 6.20 | 6.10 |

[1]Specimen concentration is expressed in terms of concentration after mixing of specimen with viral solution in equal amounts.
[2]ND: Not detected. Even when sample was inoculated without dilution after sensitization, infective virus cannot be detected.
[3]Control represents viral value after mixing of viral solution with PBS (−) and sensitizing.

REFERENCE EXAMPLE 3

Effect of specimens upon plant pathogenic virus was inspected.

A. Testing Materials (1) The respective 200 times dilution aqueous solutions and 1,000 times dilution aqueous solutions of the extract ingredient obtained in Example 1 (hereinafter abbreviated to "W ingredient"), that obtained in Example 4 (hereinafter abbreviated to "M ingredient") and that obtained in Example 2 (hereinafter abbreviated to "E ingredient") were used as sample aqueous solutions.

(2) As the plant pathogenic virus, tobacco mosaic virus (TMV) and cucumber mosaic virus (CMV) were choiced, and as plants to be tested, *Nicotiana Glutinosa*

(hereinafter abbreviated to NG) which is a wild standard strain of tobacco, was used upon TMW and cucumber was used upon CMV.

B. Testing Method

As to the viral inoculation method, 2 ppm solution was used for TMV and 100 times diluted solution, for CMV, and a suitable amount of fine powder of carborundum was added to and uniformly mixed with the respective diluted solutions, followed by allowing the mixture to adsorb on a absorbent cotton, rubbing the surface of leaf of the above plants with the cotton and having the resulting wound affected with the viruses.

As to practical infection inhibitory test, in the case of the test upon tobacco, each sample aqueous solution was applied onto a half of the leaf surface and after 3 hours, the above viral inoculation was carried out on the whole surface of the leaf. Judgement was carried out by counting the number of necrotic spots which appeared after 48 hours. Another half of the leaf surface onto which the sample solution was not applied was made a control to the above applied half.

On the other hand, in the infection inhibitory test upon cucumber, the respective aqueous solutions of the samples were applied onto the whole surfaces of leaves of several stocks excluding a control, and after 13 hours, the above viral inoculation was carried out on the whole surfaces of leaves. Judgement was carried out by counting the number of stocks having a heavy appearance of the necrotic spots, a slight appearance thereof and no appearance thereof after 48 hours.

C. Conclusion

The results of the infection inhibitory test upon tobacco are shown in Table 9 and those upon cucumber are shown in Table 10. Numeral values in Table 9 represent the number of necrotic spots and those in Table 10 represent the number of stocks.

Any cases in Table 9 notably demonstrate the effectiveness of the viral agent of the present invention.

Table 10 demonstrates that 100 times diluted solution of the antiviral agent of the present invention is effective.

TABLE 9

Infection inhibitory test upon tobacco

| No. of stocks | Test No. 1 | | Test No. 2 | | Test No. 3 | | Test No. 4 | | Test No. 5 | | Test No. 6 | |
|---|---|---|---|---|---|---|---|---|---|---|---|---|
| | C[1] | W-200[2] | C | M-200[2] | C | E-200[2] | C | W-1000[2] | C | M-1000[2] | C | E-1000[2] |
| 1 | 132 | 0 | 70 | 0 | 96 | 1 | 96 | 0 | 134 | 2 | 100 | 1 |
|   | 121 | 2 | 81 | 1 | 68 | 1 | 87 | 2 | 116 | 1 | 113 | 0 |
|   | 116 | 0 | 87 | 0 | 57 | 0 | 94 | 0 | 140 | 3 | 142 | 0 |
| 2 | 59 | 0 | 90 | 0 | 93 | 0 | 88 | 0 | 95 | 0 | 115 | 0 |
|   | 48 | 0 | 112 | 0 | 80 | 0 | 95 | 0 | 76 | 0 | 138 | 2 |
|   | 67 | 0 | 75 | 0 | 72 | 0 | 98 | 0 | 68 | 0 | 71 | 0 |
| 3 | 70 | 0 | 133 | 0 | 81 | 0 | 67 | 2 | 74 | 1 | 136 | 0 |
|   | 28 | 0 | 114 | 0 | 121 | 0 | 96 | 2 | 91 | 1 | 81 | 0 |
|   | 56 | 0 | 130 | 0 | 77 | 0 | 81 | 2 | 88 | 0 | 87 | 0 |

[1] C represents control.
[2] The letters W, M and E on the left side represent W ingredient, M ingredient and E ingredient, respectively, and the numerals on the right side represent the dilution magnification of aqueous solutions, respectively.

TABLE 10

Infection inhibitory test upon cucumber

| | Appearance of necrotic spots | | | Total number of stocks |
|---|---|---|---|---|
| | Heavy | Slight | None | |
| Control | 11 | 1 | 0 | 12 |
| W-100[1] | 2 | 5 | 2 | 9 |
| M-100[1] | 2 | 6 | 1 | 9 |
| W-1000[1] | 8 | 1 | 0 | 9 |
| M-1000[1] | 8 | 1 | 0 | 9 |

[1] The letters W and M on the left side represent W ingredient and M ingredient, respectively. The numerals on the right side represent the dilution magnification of aqueous solutions, respectively.

What we claim is:

1. A dry ingredient obtained by
   (1) milling the whole or the rhizome of *crocosmia x crocosmaeflora* N.E. Br. and subjecting it to extraction with a solvent selected form the group consisting of water, lower aliphatic alcohols and mixtures of the foregoing, at a temperature of from 0° C. to the boiling points of said solvent,
   (2) filtering the resulting material and recovering the resulting filtrate,
   (3) concentrating the filtrate, and
   (4) filtering off any white precipitate that is formed, and
   (5) drying the resulting solution to obtain the dry ingredient.

2. The dry ingredient according to claim 1 wherein said extraction is carried out with water.

3. The dry ingredient according to claim 2 wherein said extraction is carried out with water under boiling conditions.

4. The dry ingredient according to claim 1 wherein said extraction is carried out with a lower aliphatic alcohol.

5. The dry ingredient according to claim 4 wherein said lower aliphatic alcohol is ethanol.

6. The dry ingredient according to claim 4 wherein said lower aliphatic alcohol is methanol.

7. The dry ingredient according to claim 1 wherein said extraction is carried out with a mixture of water and a lower aliphatic alcohol.

8. The dry ingredient according to claim 7 wherein said lower aliphatic alcohol is ethanol.

9. An extraction solution obtained by
   (1) milling the whole or the rhizome of *crocosmia x crocosmaeflora* N.E. Br. and subjecting it to extraction with a solvent selected from the group consising of water, lower aliphatic alcohols and mixtures of the foregoing, at a temperature of form 0° C. to the boiling points of said solvent, (2) filtering the resulting material and recovering the resulting filtrate, (3) concentrating the filtrate, and (4) filtering off any white precipitate that is formed to thereby obtain the extract solution.

10. An extract solution according to claim 9 wherein said extraction is carried out with water.

11. An extract solution according to claim 10 wherein said extraction is carried out with water under boiling conditions.

12. An extract solution according to claim 9 wherein said extraction is carried out with a lower aliphatic alcohol.

13. An extract solution according to claim 12 wherein said lower aliphatic alcohol is ethanol.

14. An extract solution according to claim 12 wherein said lower aliphatic alcohol is methanol.

15. An extract solution according to claim 9 wherein said extraction is carried out with a mixture of water and a lower aliphatic alcohol.

16. An extract solution according to claim 15 wherein said lower aliphatic alcohol is ethanol.

* * * * *